United States Patent [19]

Ganguly et al.

[11] 3,975,372

[45] Aug. 17, 1976

[54] PREPARATION OF 12,13-DESEPOXY-12,13-DEHYDROROSAMICIN

[75] Inventors: Ashit K. Ganguly, Upper Montclair; Olga Sarre, Verona, both of N.J.

[73] Assignee: Schering Corporation, Kenilworth, N.J.

[22] Filed: Feb. 28, 1975

[21] Appl. No.: 554,266

[52] U.S. Cl. ................................................. 536/17
[51] Int. Cl.² ........................................ C07H 17/08
[58] Field of Search............ 260/210 AB, 239.55 R, 260/210 E

[56] References Cited
UNITED STATES PATENTS 3,657,227   4/1972   Wightman et al.......... 260/239.55 R

OTHER PUBLICATIONS

Wagman et al. "Jour. of Antibiotics" vol. XXV, No. 11, pp. 641–643, 1972.

*Primary Examiner*—Johnnie R. Brown
*Attorney, Agent, or Firm*—Carver C. Joyner; Raymond A. McDonald; Stephen B. Coan

[57]            ABSTRACT

Described is a novel process for the preparation of 12,13-desepoxy-12,13-dehydrorosamicin by reducing rosamicin in a mineral acid solution containing $Cr^{++}$ cations. Rosamicin is an antibiotic elaborated by *Micromonospora rosaria*.

7 Claims, No Drawings

PREPARATION OF 12,13-DESEPOXY-12,13-DEHYDROROSAMICIN

This invention relates to an improved process for converting rosamicin to 12,13-desepoxy-12,13-dehydrorosamicin.

DESCRIPTION OF THE PRIOR ART

Rosamicin, formerly known as Antibiotic 67-694 which antibiotic and certain derivatives thereof are described in British Pat. No. 1,302,142, granted May 2, 1973, entitled *Antibiotic 67-694 and Methods for Production Thereof*. Rosamicin is elaborated by *Micromonospora rosaria* which is also described in the aforementioned British Patent. Rosamicin has the following structural formula:

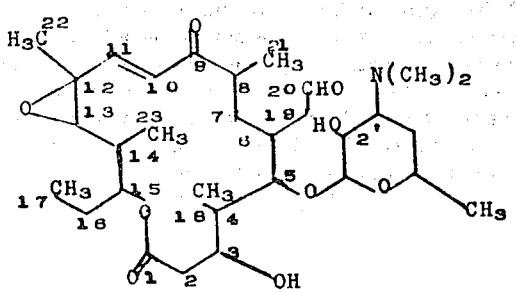

I

As can be seen from Formula I, rosamicin is a dihydroxy compound having one hydroxyl group at the 3-position of the macrolide ring and another at the 2'-position of the glycosidically linked sugar moiety. Both hydroxyl groups are susceptible to esterification. However, it is the group at the 2'-position which is first to react. Thus, in order to form a 3-monoester, it is necessary to esterify both hydroxyl groups and employ a selective hydrolysis to remove the 2'-ester function. South African Pat. No. 74/8630 granted Aug. 16, 1974 entitled: *Novel Monoesters of Rosamicin*, describes such a hydrolysis.

In an application being filed herewith which is entitled, *Novel Antibiotic Substances Derived from Rosamicin* (Attorney Docket No. 2-C.Q.Case 2087), Ser. No. 554,250 filed, Feb. 28, 1975, Hans Reimann et al. describe processes for converting rosamicin to a number of derivatives. Among the derivatives prepared is 12,13-desepoxy-12,13-dehydrorosamicin. According to the Reimann et al. process, rosamicin is dissolved in an organic acid, e.g. (acetic acid) and treated with an alkali metal iodide, preferably potassium iodide at elevated temperatures for about one hour until a composition of matter containing 12,13-desepoxy-12,13-dehydrorosamicin is formed, separating the reaction product, and isolating the individual compounds so produced by chromatography.

In effecting the Reimann et al. process, it is necessary to heat the reaction mixture to the reflux temperature in an acidic medium thereby risking the decomposition of the starting material and/or the decomposition of the product. Thus, it is not surprising that the Reimann et al process gives yields of from about 30% to about 50% of theory and consists of substantial amounts of both the cis and trans isomers. We have discovered a novel process whereby rosamicin may be converted to 12,13-desepoxy-12,13-dehydrorosamicin in yields of about 85% to 95%, said compound being about 90% pure. Further, our process yields a product which is rich in the trans isomer and, therefore, does not require chromatographic separation of the isomers.

DESCRIPTION OF THE INVENTION

The invention in its process aspect resides in a process for converting rosamicin to 12,13-desepoxy-12,13-dehydrorosamicin which comprises reducing rosamicin in a mineral acid solution containing chromous ions in an oxygen free atmosphere. The reducing agent i.e. the chromous ions are advantageously supplied in the form of a solution containing a chromous salt wherein the anion is derived from a mineral acid e.g. chromous chloride, chromous sulfate, chromous iodide, or the like. The preferred reducing agent is chromous chloride which may advantageously be prepared by the procedure described in *Inorganic Synthesis*, Volume III, pages 148–150, published by McGraw-Hill (1950). It is preferred that the chromous chloride solution be freshly prepared immediately before use to mitigate against chromic ion formation.

Further, for optimum yields of the desired product, the ratio of chromous ions to rosamicin must be in the range of from 2.0 to 2.2 moles per mole. When the ratio of chromous ions to rosamicin is below 2.0, some rosamicin remains unreduced. Conversely, when the ratio of chromous ion to rosamicin is above 2.2, reduction of the product i.e. 12,13-desepoxy-12,13-dehydrorosamicin occurs.

The mineral acids useful for effecting this process are hydrohalic (e.g. hydrochloric), phosphoric, nitric and, preferably, sulfuric. Further, it is preferred that the strength of the acid be from about 0.5N to about 3.0N, preferably about 1.0N. The concentration of rosamicin in the reaction mixture may be varied over a substantial range, provided the pH of the reaction mixture does not exceed 2.0 and, preferably is maintained at a pH of about 1.0. Rosamicin being basic reacts with one equivalent of acid per mole thereby raising the pH of the reaction mixture. The preferred concentration of rosamicin in the reaction mixture is about 125–175 mgs/ml.

The reaction proceeds at temperatures of from about 10°C to about 40°C, about 25°C being preferred. The reaction may be allowed to proceed from about 8 to about 24 hours with about 15 to 20 hours being preferred.

After conversion of rosamicin to 12,13-desepoxy-12,13-dehydrorosamicin is complete, the product is isolated by conventional means, preferably by extracting with a water immiscible organic solvent then basifying the reaction mixture and re-extracting with a water immiscible organic solvent. The product is then finally isolated by evaporation of the solvent.

The following example is set forth to illustrate the best mode contemplated for effecting the process of this invention. However, it should not be construed as limiting the scope thereof.

EXAMPLE I

12,13-Desepoxy-12,13-dehydrorosamicin

Dissolve 50 gms. of rosamicin in 300 ml. of 1N sulfuric acid under argon. Add 51.5 gms. of chromic chloride hexahydrate in 80 ml. of water and 20 ml. of sulfuric acid which has been dripped through a column of 100 gms. of amalgamated zinc thereby forming an equivalent quantity of chromous ions (see *Inorganic Synthesis*, Volume 3, pages 148–150). At this point the pH of this solution should be about 0.8 to 1.2. Allow the reaction to stand at room temperature (25°C) overnight (18 hours) under argon. Extract the reaction mixture with 500 ml. of ethyl ether. Adjust the reaction mixture to pH 8 with 8N sodium hydroxide. Extract the reaction mixture with 2.0 liters of ethyl ether and filter the extract. Wash the extract with water and concentrate the extract to a residue. Dissolve the residue in ethanol: water (1:2) and lyophilize.

Yield 44.7 gms. (89.4%) $[\alpha]_D^{26.5°} = -29.3$ (C=3% $CHCl_3$) $\epsilon_{max}^{CH_3OH}$ 283 nm ($\lambda$=20, 420).

The product of the foregoing example, i.e. 12,13-desepoxy-12,13-dehydrorosamicin is active against a broad spectrum of bacteria and is especially useful against Gram-positive bacteria. Among the bacteria against which the compound is active are strains of the following species: *Staphylococcus aureus, Streptococcus pyogenes, Diplococcus pneumoniae, Bacillus subtilis, Escherichia coli, Pseudomonas aeruginosa, Proteus mirabilis* and *Proteus morganii*.

We claim:

1. A process for converting rosamicin into 12,13-desepoxy-12,13-dehydrorosamicin which comprises reducing rosamicin in a dilute mineral acid solution under an inert atmosphere containing as the reducing agent chromous ions derived from the chromous salt of a mineral acid.

2. A process as defined in claim 1 wherein the chromous ions are present in the range of from 2.0 to 2.2 moles per mole of rosamicin.

3. A process as defined in claim 1 wherein the dilute mineral acid solution is from about 0.5N to about 3N.

4. A process as defined in claim 1 wherein the reaction medium is maintained at from about 10°C to about 40°C.

5. A process as defined in claim 1 wherein the reduction is allowed to proceed for from about 8 to about 24 hours.

6. A process according to claim 1 wherein the reaction mixture is maintained between pH 0.8 and 2.

7. The process for converting rosamicin to 12,13-desepoxy-12,13-dehydrorosamicin which comprises reducing rosamicin at 25°C in 1N sulfuric acid under argon with chromous ions derived from chromous chloride wherein the mole ratio of chromous chloride to rosamicin is 2.2 to 1 and wherein the reduction is allowed to proceed for about 18 hours.

* * * * *